(12) United States Patent
Keiller et al.

(10) Patent No.: US 11,414,262 B2
(45) Date of Patent: Aug. 16, 2022

(54) BICYCLE TRANSPORT CONTAINER AND INSIDE-LEG MEASUREMENT SYSTEM

(71) Applicant: Canyon Bicycles GmbH, Koblenz (DE)

(72) Inventors: John Keiller, Manchester (GB); Bryn Daniel Morgan, Arnside (GB); Henry Alexander James, Manchester (GB)

(73) Assignee: Canyon Bicycles GmbH, Koblenz (DE)

( * ) Notice: Subject to any disclaimer, the term of this patent is extended or adjusted under 35 U.S.C. 154(b) by 92 days.

(21) Appl. No.: 16/931,580

(22) Filed: Jul. 17, 2020

(65) Prior Publication Data

US 2020/0346848 A1    Nov. 5, 2020

Related U.S. Application Data

(62) Division of application No. 15/943,851, filed on Apr. 3, 2018, now abandoned.

(30) Foreign Application Priority Data

Apr. 5, 2017    (DE) ..................... 20 2017 001 816.0

(51) Int. Cl.
| | |
|---|---|
| *B65D 85/68* | (2006.01) |
| *A41H 1/02* | (2006.01) |
| *G01B 5/00* | (2006.01) |
| *G01B 5/06* | (2006.01) |
| *A61B 5/107* | (2006.01) |
| *B62H 3/08* | (2006.01) |
| *B65D 5/50* | (2006.01) |
| *B65D 88/12* | (2006.01) |

(52) U.S. Cl.
CPC ............... *B65D 85/68* (2013.01); *A41H 1/02* (2013.01); *A61B 5/1072* (2013.01); *B62H 3/08* (2013.01); *B65D 5/5028* (2013.01); *B65D 88/127* (2013.01); *G01B 5/0025* (2013.01); *G01B 5/061* (2013.01); *B65D 2585/6862* (2013.01)

(58) Field of Classification Search
CPC ............ B65D 85/68; B65D 2585/6862; B65D 5/5028; B65D 88/127; A41H 1/02; A61B 5/1072; B62H 3/08
USPC ............................ 206/335; 33/494, 512, 712
See application file for complete search history.

(56) References Cited

U.S. PATENT DOCUMENTS 2,339,947 A * 1/1944 Reaume ................ B65D 85/68
    206/335
2,609,091 A   9/1952 Rothe et al.
(Continued)

FOREIGN PATENT DOCUMENTS

| DE | 905125 C | 2/1954 |
|---|---|---|
| DE | 1677522 U | 6/1954 |

(Continued)

*Primary Examiner* — Luan K Bui
(74) *Attorney, Agent, or Firm* — The Webb Law Firm

(57) ABSTRACT

A bicycle transport container, particularly a bicycle transport box, includes an outer container. Within the outer container, a base element, is arranged. The base element serves for accommodating an at least partially pre-mounted bicycle. The base element includes a bottom element which is supported on a bottom portion of the outer container. The outer container includes an openable side portion so that the base element together with the bicycle can be laterally pulled out from the outer container.

19 Claims, 5 Drawing Sheets

(56) References Cited

U.S. PATENT DOCUMENTS

| | | | |
|---|---|---|---|
| 2,629,487 A | 2/1953 | Kells et al. | |
| 3,929,225 A * | 12/1975 | Locke | B65D 5/5038 |
| | | | 206/335 |
| 4,149,634 A | 4/1979 | Lewis, Jr. et al. | |
| 4,694,581 A * | 9/1987 | Heinrich | G01B 5/061 |
| | | | 33/832 |
| 4,928,398 A | 5/1990 | Delfiner | |
| 5,491,907 A | 2/1996 | Vidmar | |
| 5,669,497 A | 9/1997 | Evans et al. | |
| 6,073,359 A * | 6/2000 | Lee | A61B 5/1072 |
| | | | 33/DIG. 1 |
| 6,226,881 B1 | 5/2001 | Landauer | |
| 6,267,237 B1 * | 7/2001 | McNeill | B65D 85/68 |
| | | | 53/445 |
| 7,181,861 B1 * | 2/2007 | Leser | G01B 5/061 |
| | | | 33/832 |
| 8,869,415 B1 * | 10/2014 | Haykeen | A61B 5/1072 |
| | | | 33/485 |
| 9,389,056 B2 | 7/2016 | Wood | |
| 2017/0066588 A1 | 3/2017 | Schreiber et al. | |

FOREIGN PATENT DOCUMENTS

| | | |
|---|---|---|
| DE | 2407153 A1 | 8/1975 |
| DE | 29516898 U1 | 12/1995 |
| DE | 10205547 A1 | 8/2003 |
| DE | 102015116432 A1 | 3/2017 |
| EP | 2239210 A1 | 10/2010 |
| FR | 2729123 A1 | 7/1996 |
| JP | 58136104 U | 9/1983 |
| JP | 07215389 A | 8/1995 |
| JP | 2013212875 A | 10/2013 |
| TW | M400997 U1 | 4/2011 |

* cited by examiner

BICYCLE TRANSPORT CONTAINER AND INSIDE-LEG MEASUREMENT SYSTEM

CROSS-REFERENCE TO RELATED APPLICATIONS

This application is a divisional of U.S. patent application Ser. No. 15/943,851 filed Apr. 3, 2018, which claims priority to German Patent Application No. 20 2017 001 816.0 filed Apr. 5, 2017, the disclosures of which are hereby incorporated in their entirety by reference.

BACKGROUND OF THE INVENTION

Field of the Invention

The invention relates to a bicycle transport container, particularly a bicycle transport box. The invention further relates to an inside-leg measurement system which preferably is integrated into the bicycle transport container.

Description of Related Art

For transport purposes, particularly for the conveyance of bicycles, it is known to use bicycle transport containers, particularly bicycle transport boxes made e.g. of cardboard. To allow for shipment by transport companies such as e.g. DHL or UPS, such transport containers must have a defined high stability and must not exceed a maximum size. A bicycle transport container suited for this purpose is described e.g. in EP 2 239 210. Using such a transport container, bicycle frames, while in a partially pre-assembled state, can be reliably shipped together with the non-mounted wheels. Provided that the bicycle transport container is handled in the conventional manner, no damage will be caused to the bicycle during transport.

Said bicycle transport container described in EP 2 239 210 comprises an outer container and respectively an outer box made of cardboard. In this outer container or box, specially designed accommodating elements, preferably likewise made of cardboard, are arranged for accommodating the rear stay of the bicycle fork. The two accommodating elements are arranged on a bottom end of the outer container. For removal of the pre-assembled bicycle frame and the two wheels, the outer container has to be opened at its top side so that the pre-assembled bicycle frame and the wheels can be taken out in upward direction. In sports bicycle with their inherently low weight, this does not pose any problem at all. However, when using a corresponding bicycle transport container for heavy bicycles such as e.g. e-bikes, removal of the bicycle by lifting it out of the container is inconvenient.

It is an object of the invention to provide a bicycle transport container, particularly a bicycle transport box, which allows for better handling.

SUMMARY OF THE INVENTION

The bicycle transport container of the invention, which preferably is produced as bicycle transport box made of cardboard, includes an outer container. The outer container is preferably made of cardboard. Inside the outer container, a base element is arranged. The base element serves for holding the bicycle frame. With particular preference, the bicycle frame has been partially pre-assembled to the effect that the rear wheel is already mounted into place. According to the invention, the base element includes a bottom element. The bottom element is supported on a bottom portion of the outer container. It is preferred that the base element includes a continuous bottom element, thus particularly allowing for a face-to-face support of the bottom element on the bottom portion, i.e. on the inner side of the bottom portion of the outer container. Particularly, the outer dimensions of the bottom portion are selected to the effect that they at least partially correspond to the inner width and the inner length of the outer container. Thereby, it is avoided that, during transport, the bottom elements might happen to slide out of place in the outer container. In this regard, it is preferred, particularly for reasons of stability, that the respective bottom portion of the outer container has a rectangular cross section so that the bottom element is in abutment on the inner side of the outer container across the entire length and preferably also across the entire width.

Further, the preferably parallelepipedic outer container is designed with an openable side portion. In case of a parallelepipedic outer container, this component preferably is the side portion that has the smaller width. This less wide side portion can be opened e.g. in the manner of a door. The side portion herein, which particularly is the side portion of the front side, is connected, along a vertical longitudinal edge, to one of the two larger side portions extending in the longitudinal direction of the box. This is particularly the bending edge of the box. On the opposite side, with the aid of a corresponding flap, an adhesive tape and the like, the openable side portion can be fixed for transport. By opening the side portion, the base element together with the bicycle held or supported by it can be laterally pulled out from the outer container. The base element herein corresponds to a kind of platform on which the preferably pre-assembled bicycle is arranged. Removal of the bicycle from the outer container in upward direction will not be required anymore.

Particularly, the pre-assembled bicycle is arranged on the base element in such a manner that the bicycle is, one the one hand, held by the base element, while, on the other hand, it is at least largely not surrounded by the base element. Thus, once the base element has been pulled out together with the bicycle from the outer container, it will be possible in a simple manner to remove the bicycle from the base element in a lateral direction. As a result, also heavy bicycles can be easily taken out from the outer container. Of course, this is of advantage also in case of bicycles having a low weight.

According to a preferred embodiment of the invention, the base element includes a recess for accommodating the preferably pre-assembled rear wheel. Said recess is preferably of a slotted shape and extends substantially in the longitudinal direction of the base element. Thus, for transportation, the rear wheel can be placed in the recess from above. Particularly, the recess has a height in the range from 4 cm to 8 cm, thus providing for safe hold of the rear wheel in the recess.

Further, it is preferred that said element includes a recess for accommodating the steertubes. This arrangement can be provided in the form of two separate recesses or one common recess for both steer tube ends. For transport, the steertube ends will be inserted from above into the preferably two recesses and thus will be fixed in position. Also here, the steertube ends will be inserted into the recess by 4 cm to 8 cm, thus guaranteeing a safe hold of the steertube ends in the base element. Preferably, the two recesses for the steertube ends are arranged substantially behind each other in the longitudinal direction of the base element. For transport, the front wheel fork will be rotated by 90° relative to the conventional orientation so that the bicycle handlebar— likewise preferably pre-assembled—will extend substantially parallel to the longitudinal direction of the frame.

Further, it is preferred to provide a recess in the base element for accommodating a non-mounted front wheel. Also this recess preferably is a slot-shaped recess, preferably extending in the longitudinal direction of the base element. Again, the height of the recess is 4 cm to 8 cm so that also the front wheel can be safely arranged in the recess. Particularly, the recess for the front wheel is arranged beside the recesses for the steertube ends so that, for transport, the front wheel is arranged laterally beside a top tube and a down tube of the bicycle frame. For stabilization, the front wheel can further be connected to the bicycle frame via holding elements designed e.g. as bands.

According to a further preferred embodiment, the base element includes preferably two side elements arranged at least partially laterally of the pre-mounted rear wheel or laterally of the rearstay of the bicycle frame. The side elements herein are preferably an integral part of the base elements, wherein the base element is preferably made from a flat blank by kinking and assembling. Particularly, the base element is produced from a cardboard blank. The side elements herein are preferably arranged in such a manner that they have a mutual distance which corresponds to the inner width of the outer container. Thus, for transport, the side elements are in abutment on the inner side of the side elements of the outer container. When the base element is pulled out from the outer container, the side elements will thus slide on the inner side of the side elements of the outer container By such arrangement of the side elements, an additional stiffening effect is realized for the transport container.

Thus, it is further preferred that two mutually opposite side elements are provided which, for stiffening, are additionally connected to at least one end side element. The end side element again has a width corresponding to the inner width of the outer container and, during transport, will be in abutment on the end side elements of the outer container on the inner side thereof. It is particularly preferred that one can pull out the base element from the outer container by gripping the end side element. For this purpose, the end side element can include grip recesses.

According to a further preferred embodiment, a connection element is provided for added stiffening effect. Also said connection element is preferably made of cardboard. Particularly, the connection element is substantially formed as a parallelepipedic receiving element. The connection element is suited to take up small parts such as bicycle pedals, tools etc. for transport. The connection element is preferably arranged in such a manner that it is connected to both side elements. Particularly, the connection element again has a width that corresponds to the inner width of the outer container. Further, it is preferred that the connection element is additionally connected to the at least one end side element. In this manner, an inherently stable base element is realized which is of particular advantage when it is being pulled out from the outer container.

According to a further preferred embodiment of the bicycle transport container, there is additionally provided a holding element. Again, according to a preferred embodiment, said holding element has a width that corresponds to the inner width of the outer container. The holding element is preferably arranged in the area of the bicycle fork and respectively in the area of a bicycle handlebar connected to the bicycle fork. Thus, by the holding element, the preferably pre-assembled bicycle frame can be fixed, in its front area, within the outer container. For this purpose, according to a further preferred embodiment, the holding element includes a recess for receiving the handlebar. Further, it can be provided that the holding element includes a preferably slot-shaped recess for receiving the front wheel. This slot-shaped recess is preferably arranged, for transport of the bicycle, opposite to the slot-shaped recess for the front wheel in the base element.

The invention particularly relates to a bicycle transport container together with a bicycle frame arranged in the outer container and held by the base element. Particularly, there is not only included the bicycle frame as such but an at least partially pre-assembled bicycle.

A further problem, which is generally independent from the type of the bicycle transport container and from the problems occurring during transport, is encountered in the setting of the saddle height. The saddle height is to be set particularly in dependence on the inside leg height so that, when the pedals are being pushed, there is, on the one hand, guaranteed an approximately full stretching of the leg while, on the other hand, it is avoided that the cyclist's buttocks will laterally move or slide to and fro on the saddle. A further object in delimitation over the state of the art, which is independent from the bicycle transport container, resides in the provision of an inside-leg measurement system which can be easily handled.

The above object is achieved by an inside-leg measurement system according to the invention.

The inside-leg measurement system of the invention which, with respect to the bicycle transport container, represents an independent invention, includes a base element. In the base element, a vertically oriented slot is provided. At least on one side, i.e. to the left or to the right of said slot, a seat-height scale is provided on a surface of the base element. A corresponding scale can be provided particularly on the seatpost supporting the saddle. This scale is in relation to the scale on the base element. The inside-leg measurement system of the invention further includes a measuring element. The measuring element includes a guiding projection which can be inserted into the slot, thus allowing for vertical displacement of the measuring element in the base element. The measuring element further includes a measuring projection, connected to said guiding element, for measuring the inside leg length. For measurement of the inside leg length of a user, the guiding projection will be inserted into the slot of the base element so that the measuring projection of the measuring element is arranged between the legs of the user. For measuring the inside leg length, the measuring projection will then be guided as far as possible upward between the user's legs. On the basis of this position, it will then be possible to determine a seat height with the aid of the seat height scale. In this respect, the seat height scale can include a number or indication which corresponds or is related to the appertaining number or indication on the seatpost.

According to a preferred embodiment, different scales are arranged on both sides of the slot. These are dependent from the different tire sizes that are used.

According to a particularly preferred embodiment of the seat-height measuring system, the base element is produced by kinking and assembling a flat blank element. The flat blank element particularly is a blank made of cardboard element.

It is further preferred that the base element includes a bottom element and an end side element which particularly is of two-part design and preferably is connected to the bottom element. Herein, particularly in case of a two-part design of the end side element, it is preferred that the slot is arranged between the two parts of the end side element and respectively is formed by them. Particularly, it is possible, by folding the two parts of the end side elements in a corresponding manner toward the interior, to generate an inward guiding surface in the slot that is wider than the thickness of the material of the end side element itself.

Further, it is preferred that the base element includes one side element and preferably two side elements. These are preferably connected to the bottom element and/or said at least one end side element and, with particular preference, are of a one-pieced design. Particularly, for each side, there is provided a side element which is respectively connected to the bottom element and to one of the two end side elements.

According to a particularly preferred embodiment of the seat-height measuring system, the measuring element can be detached out of the base element. Particularly if the base element is made of cardboard material, it is easily possible, by providing a corresponding perforation, to design the measuring element in a manner allowing for detachment.

According to a preferred embodiment, the measuring element additionally includes an abutment element. Also the connection element is, according to a preferred embodiment, detachable out of the base element. Further, it is preferred that the connection element can connected to the measuring element by being mounted to, particularly fitted into, the guiding projection and/or the measuring projection. Particularly, in this manner, a cross-shaped configuration is generated. The abutment element herein is arranged in such a manner that the guiding projection projects on one side of the abutment element and the measuring projection projects on the other side. In this arrangement, insertion of the guiding projection into the slot can proceed only until the abutment element has come to abut on an outer side of the base element, preferably on the outer side of said at least one end side element. Further, it is preferred that the abutment element is in face-to-face abutment on the corresponding outer side, thus safeguarding that an upper edge of the measuring projection will extend horizontally. Thereby, the measurement accuracy will be improved. Further, an upper side of the abutment element can be arranged and designed in a manner allowing the measuring scale to be read in a convenient way.

The guiding projection and the measuring projection are preferably of a one-pieced design.

According to a particularly preferred embodiment, the base element of the seat-height measuring system is designed and respectively advantageously modified in the same manner as the base element described above in the context of the bicycle transport container.

According to a particularly preferred embodiment, the transport container is designed in such a manner that the above described inside-leg measurement system is integrated into it. In this case, it is particularly preferred that the inside-leg measurement system is integrated into the base element of the bicycle transport container.

By way of alternative, the inside-leg measurement system of the invention, including a measuring element for insertion into a slot, can also be provided in bicycle transport containers which are not designed as described above. Further, the bicycle transport container can also be a conventional parallelepipedic box which includes a slot in an outer side of an end element or in which, in an outer side, particularly of an end element, a slot can be formed in a simple manner. Likewise, the parts of the measuring element that are detachable from a part of the bicycle transport container, particularly of the bicycle transport box, can also be detached out of a sidewall of a conventional bicycle transport container.

BRIEF DESCRIPTION OF THE DRAWINGS

A full and enabling disclosure of the present invention, including the best mode thereof, enabling one of ordinary skill in the art to carry out the invention, is set forth in greater detail in the following description, including reference to the accompanying drawing in which.

DESCRIPTION OF THE INVENTION

Figure 1:
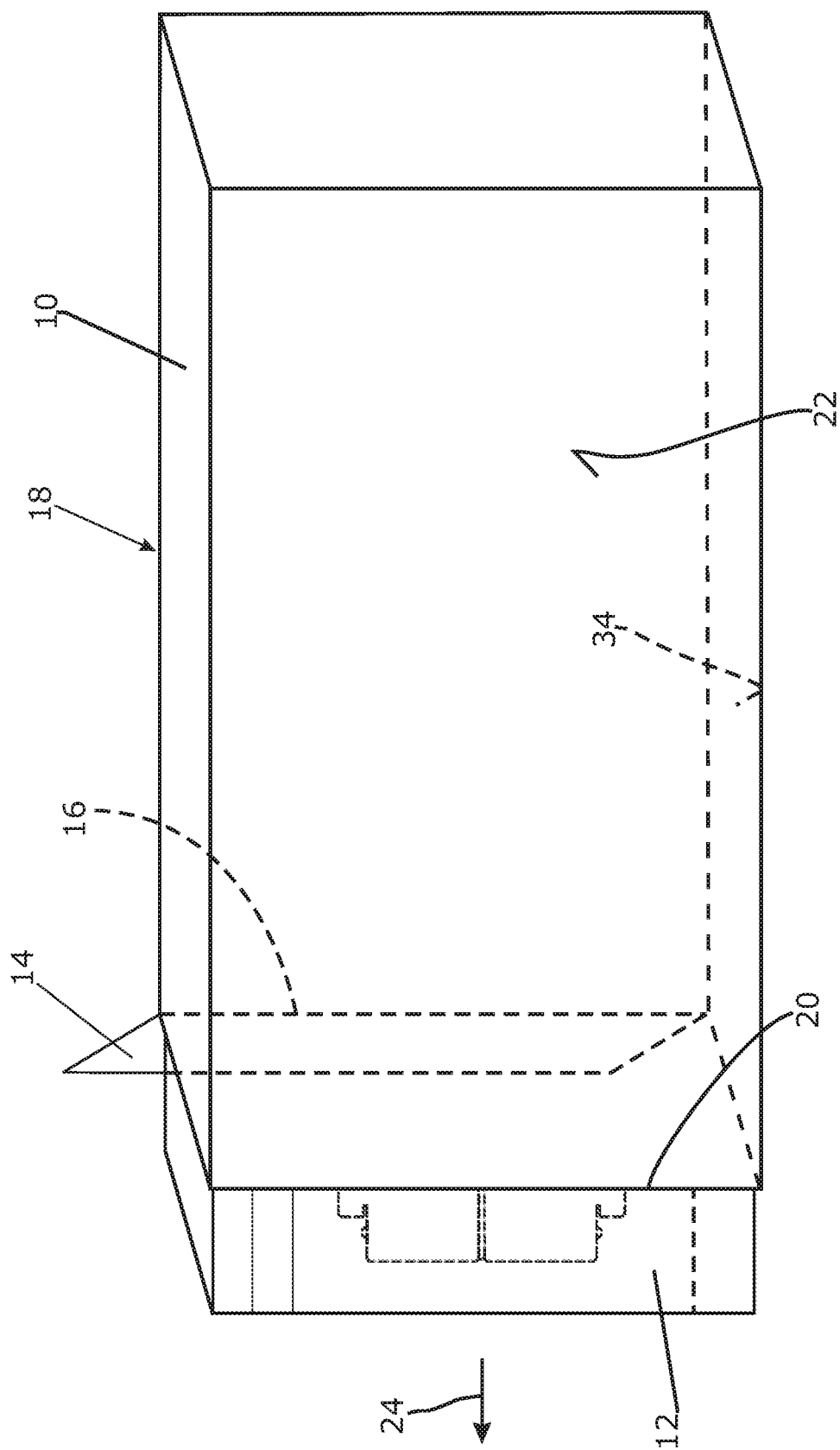
FIG. 1 is a schematic lateral view of a bicycle transport container with partially pulled-out base element.

Within an outer container, which particularly is an outer box 10, a base element 12 is arranged which in the illustrated exemplary embodiment accommodates a pre-assembled bicycle frame and a front wheel. The outer box is a parallelepipedic box comprising a side portion 14 which can be opened in the manner of a door. On a bending edge 16, the side portion 14 is connected to a side portion 18 extending in longitudinal direction. In the closed state of the box, the side portion 14 is connected to an edge 20 of the—in FIG. 1—front side portion 22 so that the box is closed. The closing can be performed with the aid of corresponding customary flaps and the like. Also, a further side portion can be provided on edge 20 so that, then, two mutually overlapping side portions 14 exist.

Figure 2:
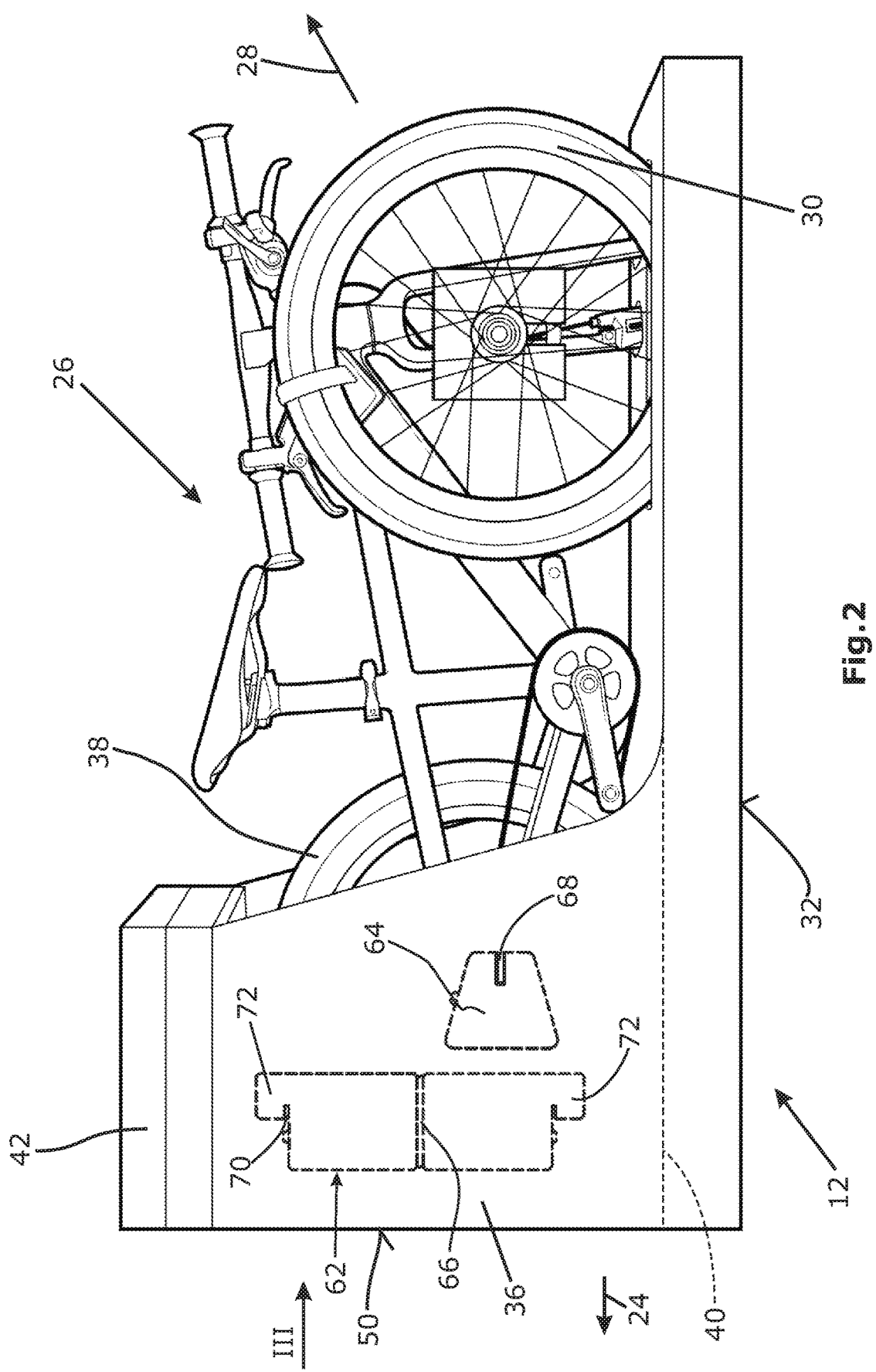
FIG. 2 is a schematic lateral view of the base element fully pulled out from the outer container.

The base element 12 supporting the pre-assembled bicycle can be pulled out from the outer box 10 in longitudinal direction. After having been pulled out, the base element is in a position as shown in FIG. 2 so that a bicycle frame 26 with pre-mounted rear wheel, pre-mounted bicycle fork and pre-mounted handlebar can be removed from the base element in a simple manner in the direction of arrow 28. Prior to this, a front wheel 30, connected to the frame via a hook-and-loop fastening device or another element, will optionally be removed from base element 12. Likewise prior to this, a box serving as a holding element (FIG. 7), not illustrated for reasons of clarity, has to be removed from the handlebar.

In the illustrated exemplary embodiment, the base element 12 comprises a bottom element 32. The bottom element 32 extends along the entire length of outer box 10 and, during pull-out, will slide in longitudinal direction 24 on a bottom portion 34 of outer box 10. The outer dimensions of bottom element 32 correspond to the inner dimensions of outer box 10, thus preventing that the base element might slide out of place within outer box 10 during transport.

Further, in the illustrated exemplary embodiment, the bottom element 32 comprises two side elements 36. When the base element has been correspondingly folded together as shown in FIG. 2, the two side elements 36 are arranged opposite to each other, wherein one rear wheel 38 is arranged at least partially between the two side elements 36. Between the rear wheel 36 and respectively rearstay of the bicycle frame and the inner sides of the side elements 36, it is possible to arrange spacers, stiffening elements, buffer elements and the like so as to guarantee a safe hold of the rear wheel in this area. Further, in a lower region between the two side elements 36, an additional box element can be provided as represented by the interrupted line 40. Said box element can comprise a recess, extending in longitudinal direction 24, in which the rear wheel 38 is arranged and thus is laterally fixed, too.

The two side elements 36 are connected to each other via a connection element 42. In the illustrated exemplary embodiment, connection element 42 is a parallelepipedic box in which e.g. the pedals, tools for assembly, the handbook etc. can be arranged. The connection element 42 is connected to the side elements 36 via flaps (FIG. 5) connected to them.

For fixation of the fork of the bicycle, the bottom element 32 comprises recesses 46 (FIG. 5), a number of two such recesses being provided in the illustrated exemplary embodiment. Into these two recesses 46, the ends of the steertubes will be inserted for transport. The bottom element 32 of base element 12 further comprises a recess 48 (FIG. 5) extending in the longitudinal direction for arrangement of the front wheel 30 in it.

Further, in the illustrated exemplary embodiment, each of the side elements 36 has an end side element 50 (FIG. 3) connected to it. For forming an end face of the base element which in the longitudinal direction 24 is arranged behind rear wheel 38, the two end sides are produced in that projections 50 (FIG. 5) are folded inward. The end side elements 50 are further connected to guiding flaps 52 which in the folded state are facing inward (FIG. 4). Between the two guiding flaps 52 and thus also between the two end side elements 50, a vertically extending slot 54 is formed. Said slot 54 serves for accommodating and respectively guiding a measuring element 56 (FIG. 6). Said measuring element together with the two measuring scales 58 serves for determining the inside leg height. The two inside leg scales 58 serve for determining the inside leg height in case of different tire diameters, wherein the left-hand scale in FIG. 3 is used for tire diameters of 16 Inches and the right-hand scale is used for tire diameters of 20 Inches while, of course, also scales for other tire diameters can be provided.

Figure 3:
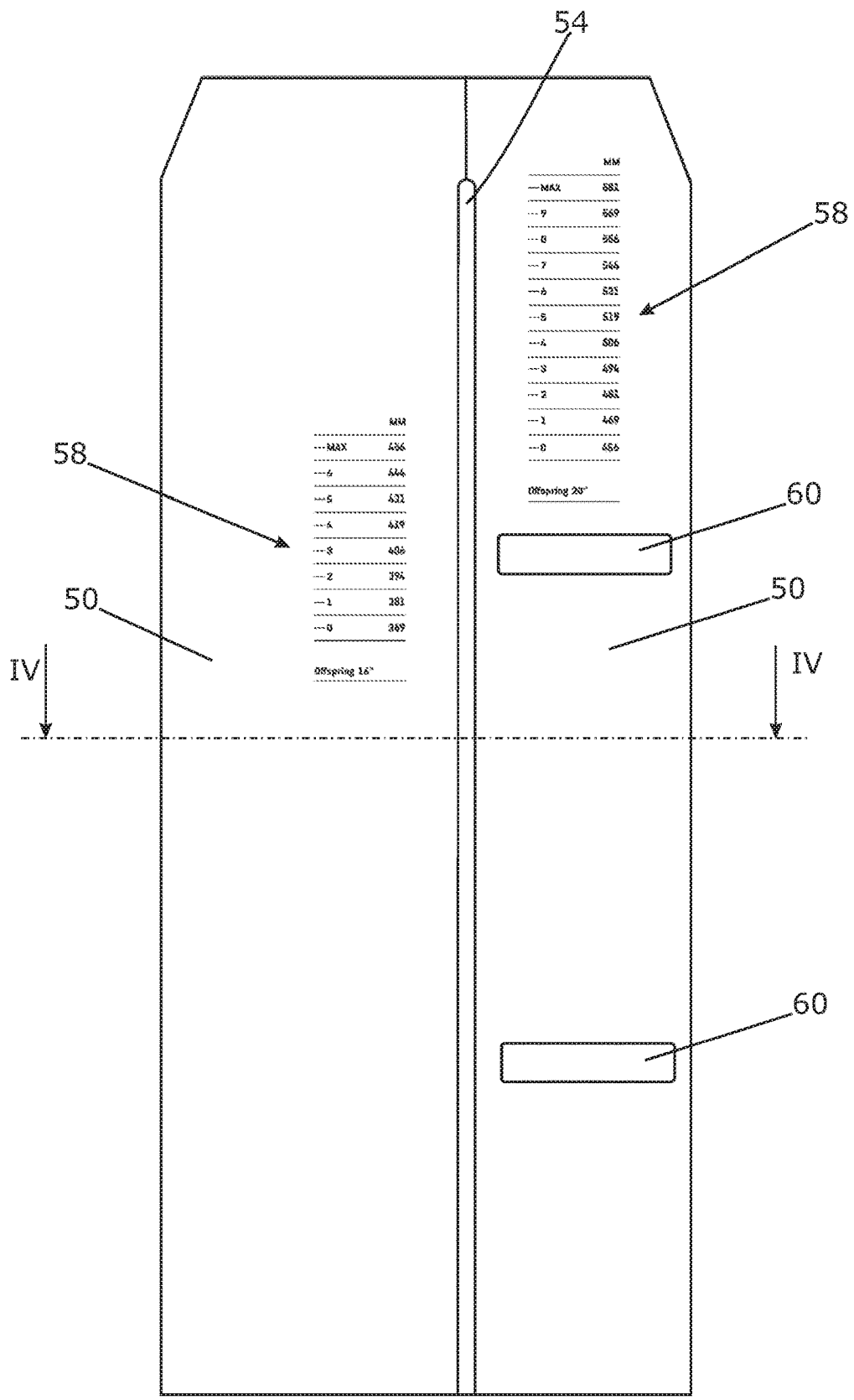
FIG. 3 is a schematic view of the end side element as seen in the direction of the arrow III in FIG. 2.
Figure 4:
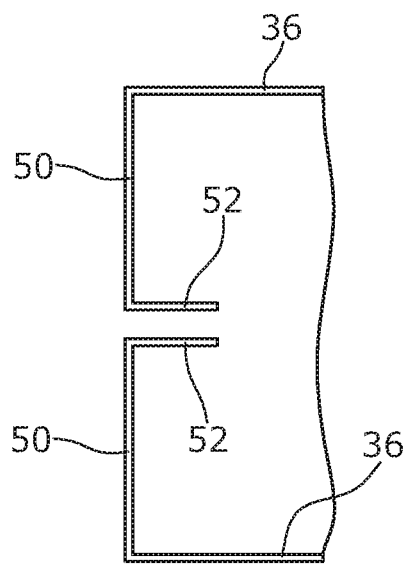
FIG. 4 is a schematic lateral view along the line IV-IV in FIG. 3.

Further, in the illustrated exemplary embodiment, two grip recesses are arranged in the end side element 50 on the right-hand side in FIG. 3. These grip recesses serve for pulling out the base element 12 from outer box 10 in longitudinal direction 24 (FIG. 1).

In the illustrated exemplary embodiment, the measuring element 56 is not a separate element. Instead, this element is produced by the user by detaching said two elements 62, 64 from one of the two side elements 36 of the base element. The corresponding areas are perforated so that the elements 62, 64 can be detached in a simple manner. The element 62 will be folded together along a centerline 66. Then, the element 64 will be guided, by means of a slot 68, into the slot 70 at a right angle. This will result in a cross-shaped element in plan view from above (FIG. 6). On the right-hand side, the element 62 herein comprises the two smaller projections which form a guiding projection 72. The left-hand portion in FIG. 6 forms a measuring projection 74. Said two projections 72,74 are separated from each other by the abutment element 76 arranged vertically to the projections.

For determining the individual inside-leg height of a user for adjustment of the saddle height, the guiding projection 72 of measuring element 56 will be inserted into the slot 54 so that one side 78 of abutment element 76 will be in abutment on an outer side 80 of the two end side elements 50. The measuring projection 74 will be arranged between the legs of the user. Subsequently, the measuring element will be shifted upward as far as possible. In dependence on the tire size, the saddle height can then be read off, with the aid of the upper edge of the abutment element 76, on the respective seat height scale 58. The scales each comprise digits on the left-hand side that are e.g. provided also on the saddle support tube supporting the saddle. This arrangement allows for easy adjustment of the saddle height in dependence on the individual inside leg height.

Figure 5:
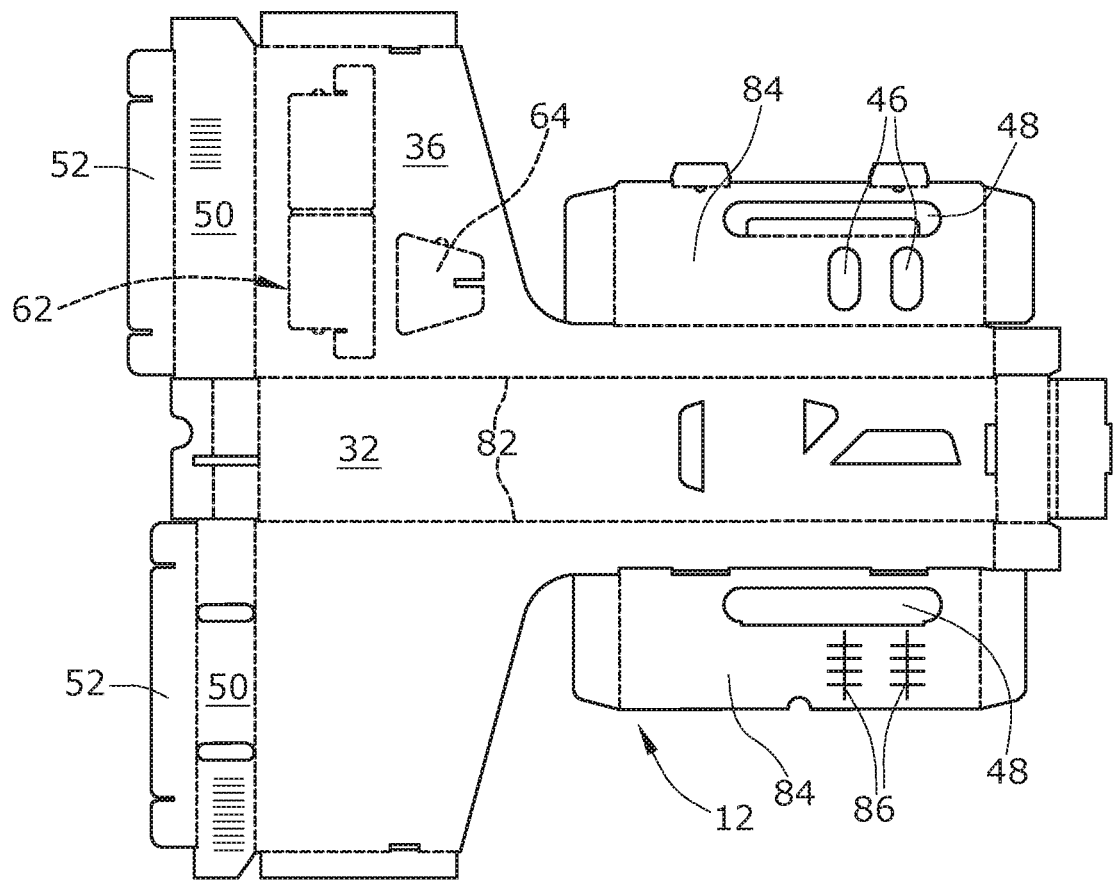
FIG. 5 is a schematic plan view of the cardboard blank of the base element.
Figure 6:
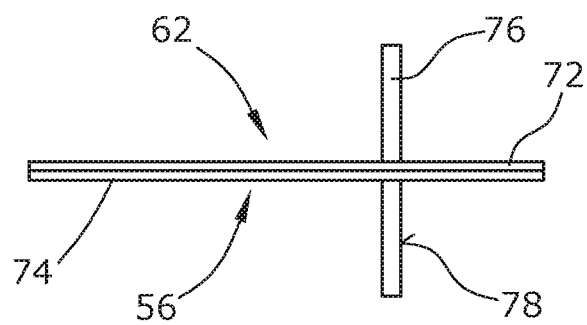
FIG. 6 is a schematic plan view of a measuring element.

For producing the base element 12, there is preferably used the cardboard blank shown in FIG. 5. Shown in FIG. 5 is the bottom side of the corresponding cardboard blank. The rectangular bottom element 32 is connected via kinking edges 82 to each of the two side elements 36. With reference to FIG. 5, these will be folded toward the rear so that the bottom element 32 and the two side elements 36 form a right angle relative to each other. Further, the two flaps 84 will be folded inward again by 90° so that the flaps 84 will be parallel to bottom element 32. On the one hand, the flaps 84 form the recess 48 for the front wheel 30 and, on the other hand, they form the recesses 46 for the two fork tube ends. For better fixation of the fork tube ends in the recesses 46, the upper flap 34 in FIG. 5 comprises cuts 86.

For forming the front side, the two end side elements 50 will be folded inward wherein, prior to this, the two flaps 52 will be folded inward by 90° again so that, in the assembled state, these extend parallel to the side elements 36 (FIG. 4).

Figure 7:
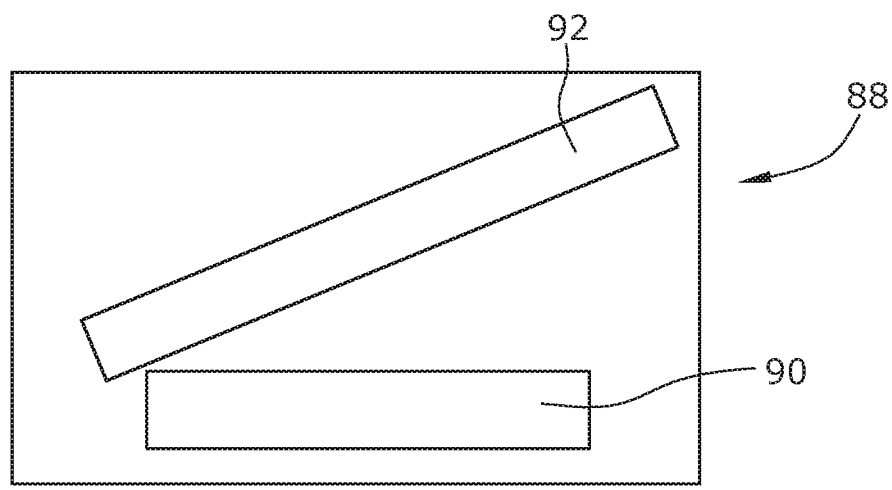
FIG. 7 is a schematic bottom view of a holding element.

FIG. 7 is a bottom view of a holding element 88. The holding element is a parallelepipedic box. This box will be arranged on the handlebar and the front wheel 30. For this purpose, the parallelepipedic holding element 88 comprises a recess 90, extending in longitudinal direction, for accommodating the front wheel 30, said recess 90 being arranged opposite to recess 48 (FIG. 5). A further recess 92 serves for accommodating the bicycle handlebar. The parallelepipedic holding element 88 has a width corresponding to the inner width of outer box 10 so that the holding element serves for lateral stabilization of bicycle frame 26 and front wheel 30 in outer box 10.

Figure 8:
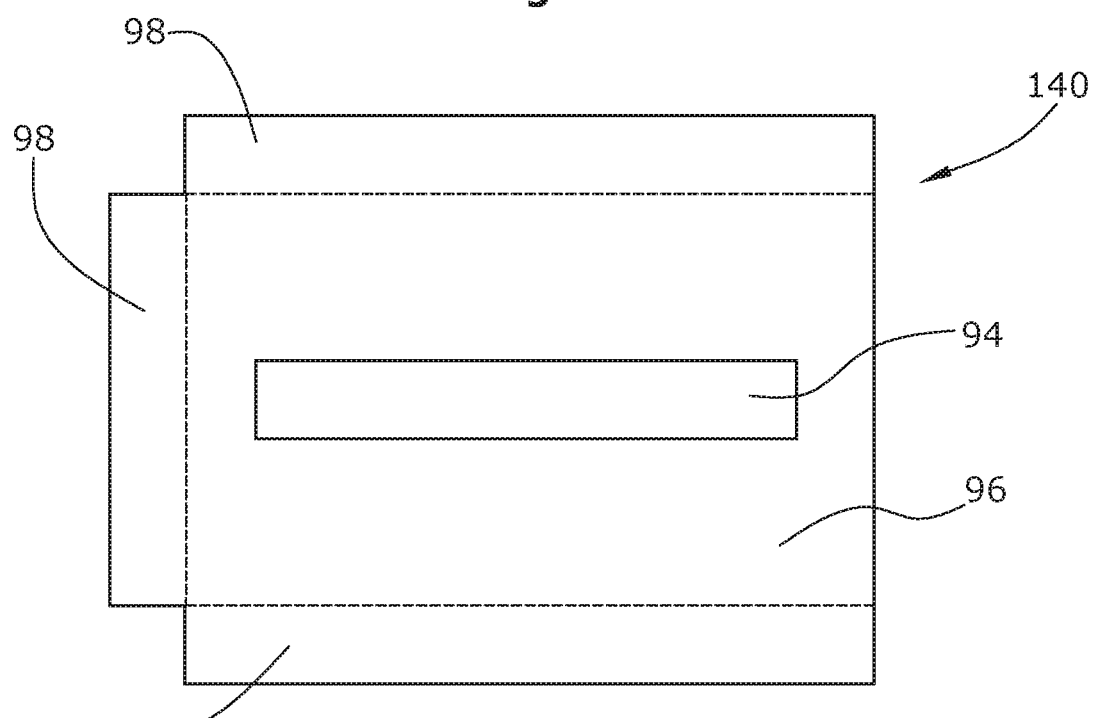
FIG. 8 is a schematic plan view of an inner component part accommodating the rear wheel.

FIG. 8 is a schematic plan view of an inner portion 40 arranged between the two side portions 36 of base element 12. Said inner portion 40 comprises a recess 94, extending in longitudinal direction 24, for accommodating the rear wheel 38. The base element 96 of inner portion 40 is rectangular and has a width which corresponds to the width of bottom element 32 and respectively of bottom portion 34. The base element 96 has three flaps 98 laterally connected to it that serve as foot support flaps and will be kinked downward. Said flaps 98 have the same height as the area of the side portions 36 at the height of the flaps 84.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A bicycle transport container, comprising:
an outer container, and
a base element, arranged within the outer container, for holding a bicycle frame with the rear wheel mounted to the bicycle frame,
wherein the base element comprises a bottom element supported on a bottom portion of the outer container,
wherein the outer container comprises an openable side portion so that the base element together with the bicycle frame can be laterally pulled out from the outer container, and
wherein the base element comprises an inside-leg measurement system, the inside-leg measurement system comprising:
a vertically extending slot formed in the base element,
a seat height scale arranged, at least on one side, laterally of the slot on a surface of the base element, and
a measuring element comprising a guiding projection, adapted to be inserted into the slot, for lateral displacement of the measuring element in the slot, and comprising a measuring projection, connected to the guiding projection, for measuring an inside leg height.

2. The bicycle transport container according to claim 1, wherein the base element comprises at least one of a recess for accommodating the rear wheel and a recess for accommodating a non-mounted front wheel and at least one recess for accommodating steertube ends.

3. The bicycle transport container according to claim 1, wherein the base element comprises two side elements arranged at least partially laterally of to the rear wheel.

4. The bicycle transport container according to claim 3, wherein, for stiffening, the side elements are connected to at least one side end element.

5. The bicycle transport container according to claim 3, wherein the side elements are connected to a connection element arranged above the rear wheel.

6. The bicycle transport container according to claim 1, wherein a holding element is provided that is arranged in the area of a bicycle fork and respectively a bicycle handlebar.

7. The bicycle transport container according to claim 6, wherein said holding element comprises a recess for accommodating the bicycle handlebar and a slot-shaped recess for accommodating the front wheel.

8. The bicycle transport container according to claim 1, further comprising a bicycle arranged in said outer container and held by said base element, with a pre-mounted rear wheel.

9. A bicycle transport container, comprising:
an outer container, and
a base element, arranged within the outer container, for holding a bicycle frame with the rear wheel mounted to the bicycle frame,
wherein the base element comprises an inside-leg measurement system, the inside-leg measurement system comprising:
a vertically extending slot formed in the base element,
a seat height scale arranged, at least on one side, laterally of the slot on a surface of the base element, and
a measuring element comprising a guiding projection, adapted to be inserted into the slot, for lateral displacement of the measuring element in the slot, and comprising a measuring projection, connected to the guiding projection, for measuring an inside leg height.

10. The bicycle transport container according to claim 9, wherein the base element is produced by kinking and assembling a plane blank element.

11. The bicycle transport container according to claim 9, wherein the base element comprises a bottom element and an end side element which is of a two-part design and is connected to the bottom element, said slot being provided in the end side element and being formed by the two portions of the end side element.

12. The bicycle transport container according to claim 11, wherein the base element comprises one or two side elements which are connected to at least one of the bottom element and said end side element.

13. The bicycle transport container according to claim 9, wherein the measuring element is detachable from the base element.

14. The bicycle transport container according to claim 9, wherein the measuring element further comprises an abutment element detachable from the base element.

15. The bicycle transport container according to claim 14, wherein the abutment element is connectable to at least one of the guiding projection and the measuring projection by fitting the abutment element and at least one of the guiding projection and the measuring projection together.

16. The bicycle transport container according to claim 9, wherein the guiding projection and the measuring projection are formed in one piece.

17. A bicycle transport container comprising:
a base element configured for holding a bicycle frame,
wherein the base element comprises an inside-leg measurement system, the inside-leg measurement system comprising:
a vertically extending slot formed in the base element,
a seat height scale arranged, at least on one side, laterally of the slot on a surface of the base element, and
a measuring element comprising a guiding projection, adapted to be inserted into the slot, for lateral displacement of the measuring element in the slot, and comprising a measuring projection, connected to the guiding projection, for measuring an inside leg height; and
wherein the base element further comprises a bottom element and an end side element which is of a two-part design and is connected to the bottom element, said slot being provided in the end side element and being formed by the two portions of the end side element.

18. The bicycle transport container according to claim 17, further comprising an outer container, wherein the base element is arranged in the outer container.

19. The bicycle transport container according to claim 17, wherein the measuring element is detachable from the base element.

* * * * *